US00PP13461P2

(12) United States Plant Patent
Vardi et al.

(10) Patent No.: US PP13,461 P2
(45) Date of Patent: Jan. 7, 2003

(54) CITRUS TREE NAMED 'NORA'

(75) Inventors: Aliza Vardi, Ramat Gan (IL); Pinchas Spiegel-Roy, Ramat-Gan (IL); Ahuva Frydman-Shani, Ramat-Gan (IL); Avraham Elchanati, Holon (IL); Hana Neumann, Hemed (IL)

(73) Assignee: State of Israel - Ministry of Agricultural and Rural Development, Tel Aviv (IL)

( * ) Notice: Subject to any disclaimer, the term of this patent is extended or adjusted under 35 U.S.C. 154(b) by 0 days.

(21) Appl. No.: 09/716,484

(22) Filed: Nov. 20, 2000

(51) Int. Cl.[7] ..... A01H 5/00
(52) U.S. Cl. ..... Plt./202
(58) Field of Search ..... Plt./202

*Primary Examiner*—Kent L. Bell
(74) *Attorney, Agent, or Firm*—Barbara S. Kitchell

(57) ABSTRACT

A new variety of mandarin citrus tree is described that is distinguished by fruit having zero or up to six seeds per fruit, flowers having anthers bearing pollen with low pollen fertility and a late ripening period.

2 Drawing Sheets

FIELD OF THE INVENTION

A new mandarin cultivar *Citrus reticulata* hybrid is described. The new variety named 'Nora' is desirable to the consumer because of the orange-red appearance of the fruit, and pleasant aroma of the juice and to commercial growers because of its zero to maximum six seeds per fruit and late ripening season (February to beginning of March).

BACKGROUND OF THE NEW PLANT

The present invention relates to a new and distinct variety of mandarin tree of the new cultivar *Citrus reticulata* hybrid developed by inventors Aliza Vardi, Pinchas Spiegel-Roy, Avraham Elchanati, Ahuva Frydman-Shani and Hana Neumann in Bet Dagan, Israel from a selection of plants grown from irradiated bud wood of the cultivar 'Norit' (unpatented).

Asexual reproduction by conventional grafting methods of the new variety in Israel by grafting has shown that the new characteristics are stabilized and permanently fixed through successive propagation.

The objective in breeding the present new tree variety, assigned the denomination 'Nora', was to obtain late ripening mandarin citrus with few or no seeds. In the spring of 1989 about 400 buds of an easy peeling mandarin cultivar, 'Norit', were irradiated at the Weizmann Institute of Science, Rehovot, Israel, by exposure to 3.5 kh of gamma radiation from a Co60 source (G.B. 150A, Atomic Energy of Canada). Troyer nucellar rootstocks were bud grafted with the individual buds of irradiated 'Norit' bud wood and labeled $mV_1$. Six to nine months after grafting the irradiated budwood, individual buds from the $mV_1$ plants were regrafted on Troyer nucellar rootstocks to establish about 500 $mV_2$ plants.

Field planting was established from container grown $mV_2$ plants in the spring of 1991 and again in 1993. The first fruits were observed in January–March 1994 and the second observation in January–March 1995.

One of the selections, designated 8/260/52, had medium size orange-red color fruit and was easy to peel. The selection was distinguished from 'Norit' by having 0–6 seeds per fruit compared with 13–25 for 'Norit' and having flowers with low pollen fertility, typically 14.5% stained with acetocarmine compared with 87% staining for 'Norit'.

SUMMARY OF THE INVENTION

Some of the characteristics of the new citrus, designated 'Nora' were compared with the parent 'Norit', as shown in Table 1.

TABLE 1

| Tree | Productivity | Size of fruit | Seeds/fruit | Pollen fertility[1] |
|---|---|---|---|---|
| 8/260/52 'Nora' | High | medium | 0–6 | 14.5% |
| 'Norit' | High | medium | 13–25 | 87% |

[1] Estimated by Acetocarmine staining

The following is a detailed description of the new mandarin citrus variety based on observations made under typical Israeli grove conditions.

The tree shape and fruit appearance is similar to that of 'Norit'. The tree is medium in size. Small thorns, 1 mm to 3 mm are usually present in the leafy part of branches, especially in their lower portion and on the lower part of fruit bearing branches. Main branches have an upright attitude and young shoots have no anthocyanin coloration at the tip.

The bearing of the tree is regular and the productivity is relatively high, about the same as for 'Norit'. The canopy is moderately dense. The bark of the young shoots is initially smooth and green gradually turning into a smooth greyed-green.

The leaves are similar to that of 'Norit'. They are lanceolate, small to medium in size. Leaf blade is firm, without undulation and slightly concave in cross section. petiols are without wings.

The characteristics of the flowering and the flower parts are similar to those of 'Norit'. Flowering for both occurs at the end of March or first half of April as measured in Bet Dagan. Both 'Nora' and 'Norit' produce about the same number of flowers and flower drop for both occurs in April. Terminal flower buds have no anthocyanin coloration. Flowers are borne singly and have an average number of stamens (about 20) with complete style development. Anther color is pale yellow. Pollen fertility is low as indicated by the observation that only 14.5% of the pollen grains were stained with acetocarmine in a test conducted at the Agricultural Research Organization, the Volcani Center, as compared with stainability of about 87% for 'Norit' pollen grain.

The fruit has few seeds, about 0 to 6 seeds, even when optimal pollination conditions are employed. This compares with about 13 to 25 seeds per fruit in 'Norit'. In other respects the fruit characteristics are in the range of the parent cv. 'Norit'. The fruit has an oblate and slightly flattened shape and is medium sized. When 50 fruits were measured, the fruit had an average weight 145.5 grams, an average height 55.4 mm, and an average diameter 72 mm The fruit has a moderately depressed stalk end. The fruit surface is usually smooth with an orange-red color, 32B on The Royal Horticultural Society of London Colour Chart, and bears an average number of conspicuous rind oil glands. Fruit ripening does not differ from outside of the canopy to the inside, but the fruit color of the outside canopy are a little brighter compared to the fruit color of the inside canopy. There is no persistence of the style and the areola is not completely developed. A navel is absent or very rare. The rind is thin and easy to peel.

The color of the albedo is white and the flesh is orange in color. The fruit contains 11–13 segments and is very juicy. The external color of the seeds (when fresh) and dry is yellowish. The internal seed coat is white and the cotyledons are greenish.

Monoembryonic seeds are present. The seed sizes, shape and texture are similar to that of the parent 'Norit'. The fruit reaches maturity late in the season as does 'Norit', which in Israel was mid-January to March. The ripening of the fruit on the tree and within the fruit is uniform. Fruit remaining on the tree does not regreen and does not begin to lose quality until end of February. If there is a heavy crop and the fruits are not picked before March it may becomes an alternate bearing (lighter crop the following season). Preharvest drop of both developed and undeveloped fruit is similar to that of the parent cv. 'Norit'. The juice has a very pleasant aroma and flavor.

DESCRIPTION OF THE PHOTOGRAPHS

Sheet 1 shows the canopy shape of a typical tree of the new variety of cultivar.

Sheet 2 shows the exterior of the variety of fruit as well as transverse midsections in a plane substantially perpendicular to the axis, illustrating a single seed in the interior of the fruit.

DESCRIPTION OF THE NEW TREE

The following is a detailed description of the new mandarin citrus variety 'Nora' based on observations made under typical Israeli grove conditions. Specific color designations set forth were determined from The Royal Horitcultural Society Colour Chart. The age of the plants at the time of the observations was four years.

Tree:

*Origin.*—Irradiation of cv. 'Norit'.

*Classification.*—Botanical: *Citrus reticulata* hybrid. Common: Mandarin citrus. Cultivar: 'Nora'.

*Shape.*—As shown in Sheet 1 with pruning over a perior of 4 years.

*Thorns.*—1–3 mm length (leafy part of branches, mostly on lower part of fruit bearing branches).

*Branching.*—Upright.

*Canopy.*—Moderately dense.

*Bark.*—Immature: smooth and green RHS 137B. Mature: smooth and greyed-green, RHS 189A.

*Leaf.*—Size: Small to medium, 64 mm length, 38 mm width. Leaf blade: Firm, slightly concave, no undulation. Petioles: Wingless and short, 12 mm in length, 2 mm in diameter, Green RHS 147B. Shape: Lanceolate. Color: Green RHS 147A (upperside); Yellow-green 147B (underside).

*Habit.*—Moderately vigorous.

*Height.*—2–3 m.

*Disease resistance.*—No particular susceptibility or resistance observed.

*Trunk diameter.*—5 cm at 20 cm above the ground.

*Winter hardiness.*—Winter temperature in Bet Dagan, Israel averages 4–7 degrees Centigrade.

Flower:

*Color.*—White 155B.

*No. of petals.*—5.

*Flowering period.*—Late March-early April in Bet Dagan, Israel.

*Flower drop.*—April.

*Stamens.*—Approximately 20.

*Anther color.*—Yellow RHS 10C.

*Pollen ferility.*—Low, 14.5% by acetocarmine staining.

*Anthocyanin coloration.*—None on terminal or flower buds.

Fruit:

*Shape.*—Oblate and slightly flattened.

*Size.*—Medium.

*Weight.*—145.5 g (average of 50 fruits).

*Height.*—55.4 mm.

*Diameter.*—72 mm.

*Skin color.*—Smooth, RHS 32B.

*Rind oil gland.*—Conspicuous, average number (30/$cm^2$).

*Style.*—No persistence.

*Navel.*—Absent.

*Rind.*—Thin and easily peeled.

*Albedo.*—Yellow RHS 13D.

*Flesh color.*—Orange RHS 25A.

*Fruit segments.*—11–13.

*Productivity.*—About 30–40 kg per tree per season.

*Time to maturity.*—2–3 months (mid-January to March).

*Fruit extract.*—(Test conducted end of January, 1997 on juice of representative sample of ripe fruit). Total soluble solids (TSS) 14.9%. Acid content: 1.44%. TSS/acid ratio 10.37. Flavor: Pleasant flavor and aroma.

Seeds:

*Color.*—External: Yellow-white RHS 158B. Internal: Grayed-orange RHS 164A.

*Cotyledons.*—Yellow-white RHS 158B.

*Embryony.*—Monoembryonic.

*Size.*—Medium (approximately 10 mm length, 5 mm width).

The tree and its fruit as described herein may vary in slight detail due to climate and/or soil conditions under which the variety is grown.

What is claimed is:

1. A new and distinct variety of *Citrus reticulata* hybrid tree substantially as herein described and shown.

* * * * *

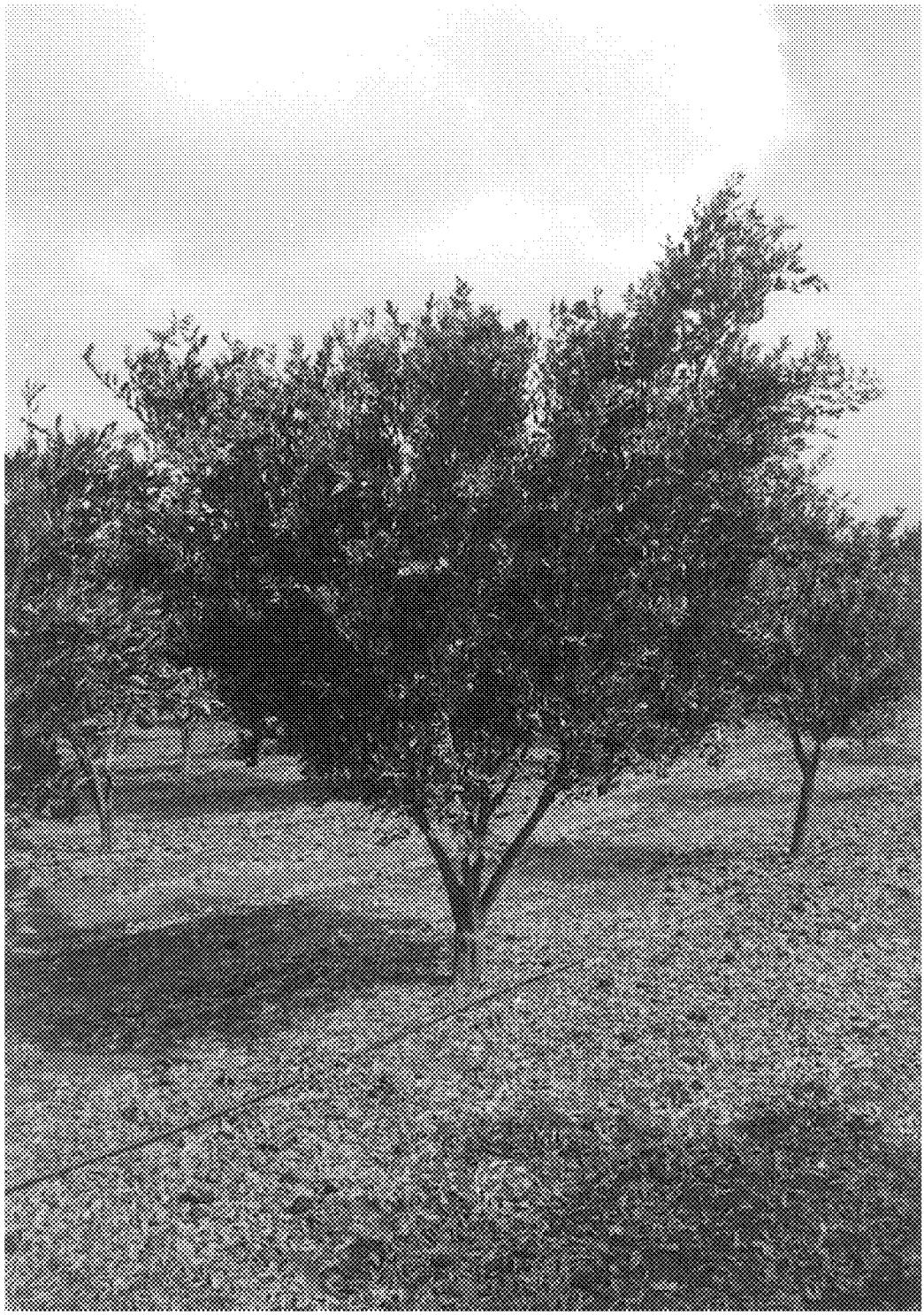

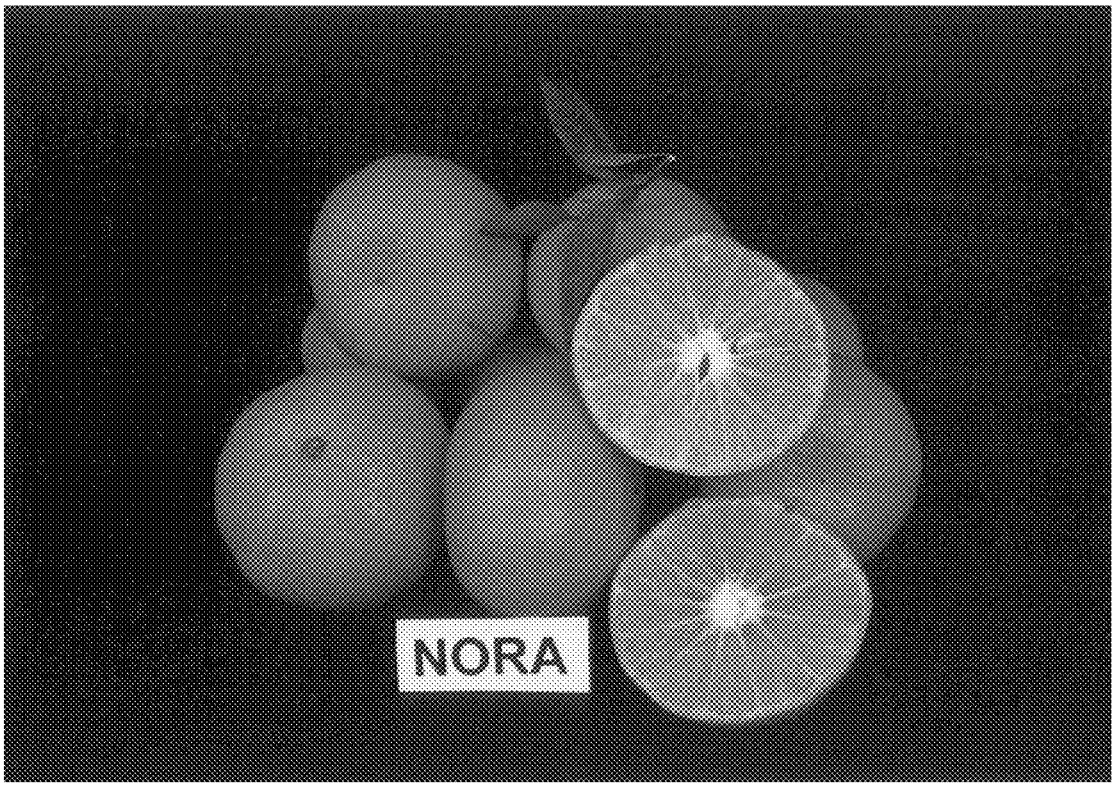
NORA